United States Patent [19]

Harrison et al.

[11] Patent Number: 5,312,537

[45] Date of Patent: May 17, 1994

[54] ELECTROCHEMICAL CELL, REFERENCE ELECTRODE AND ELECTROCHEMICAL METHOD

[75] Inventors: Michael H. Harrison; David J. Clarke, both of Salisbury, England

[73] Assignee: Public Health Laboratory Service Board, London, England

[21] Appl. No.: 838,809

[22] PCT Filed: Jul. 2, 1990

[86] PCT No.: PCT/GB90/01016

§ 371 Date: Mar. 19, 1992

§ 102(e) Date: Mar. 19, 1992

[87] PCT Pub. No.: WO91/01495

PCT Pub. Date: Feb. 7, 1991

[30] Foreign Application Priority Data

Jul. 20, 1989 [GB] United Kingdom ............... 8916633

[51] Int. Cl.$^5$ ............................................. G01N 27/26
[52] U.S. Cl. ............................ 204/416; 204/418; 204/419; 204/433; 204/435
[58] Field of Search ............... 204/412, 435, 433, 415, 204/416, 418, 419, 403

[56] References Cited

U.S. PATENT DOCUMENTS 3,707,455 12/1972 Derr et al. ...................... 204/415

FOREIGN PATENT DOCUMENTS 0021798 6/1980 European Pat. Off. .
0068025 11/1981 European Pat. Off. .
0127958 5/1984 European Pat. Off. .
0161690 5/1985 European Pat. Off. .
3242457 5/1984 Fed. Rep. of Germany .

*Primary Examiner*—John Niebling
*Assistant Examiner*—Bruce F. Bell
*Attorney, Agent, or Firm*—Browdy and Neimark

[57] ABSTRACT

The concentration of an ionic species (e.g. $K^+$) is determined using an ion sensitive electrode having an appropriate membrane (e.g. valinomycin in plasticised PVC). In place of a conventional reference electrode, the half cell is completed with an electrode having an identical membrane but lacking the constituent producing the ion-selective response (e.g. plasticised PVC). The working and reference electrodes can then be made in substantially the same manner to null of interferents. The difficulties associated with double junctions are avoided.

12 Claims, 4 Drawing Sheets

- o  Ion sensing ligand or binding site.
- ⋯ Plasticising or mediating solvent.
- ═ Coated surface with no chemical modification.
- ⁄⁄ Polymer film.
- ⋋ Chemically modified polymer.
- ⊤⊤ Chemically modified surface.

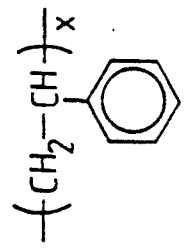
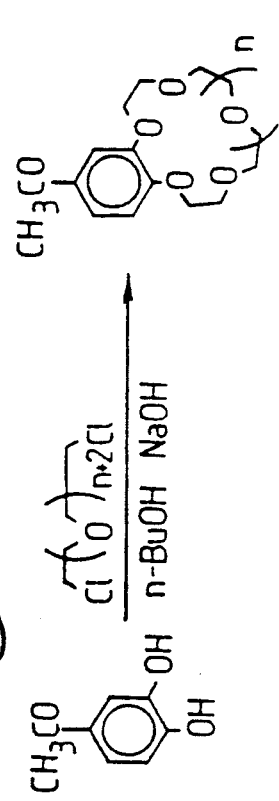
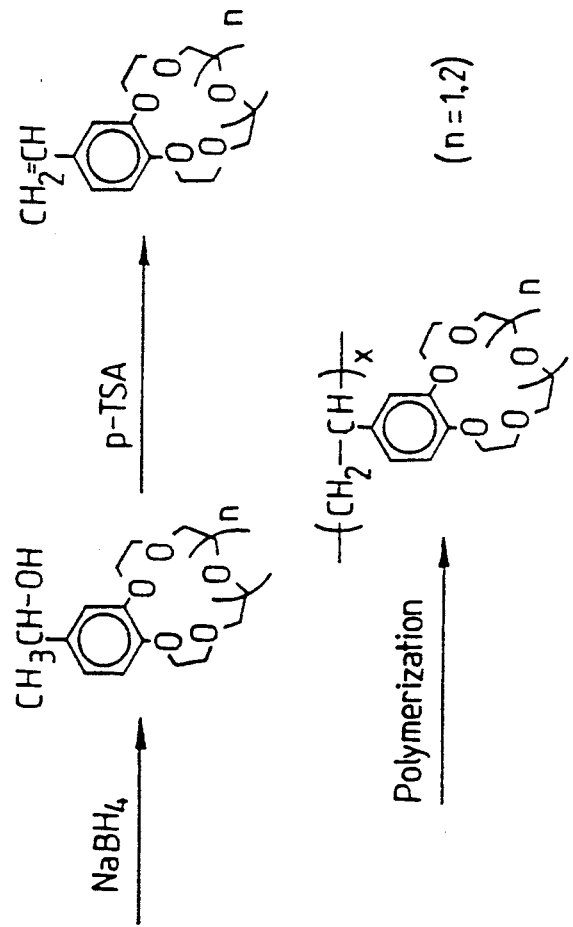
Fig.5 (a)
Fig.5 (b)

ELECTROCHEMICAL CELL, REFERENCE ELECTRODE AND ELECTROCHEMICAL METHOD

FIELD OF THE INVENTION

This invention relates to electrochemical measurements and particularly to a reference electrode for use in said measurements.

BACKGROUND OF THE INVENTION

A wide range of electrochemical methods, including amperometric and potentiometric techniques, presently use liquid filled reference electrodes.

The purpose of a reference electrode in potentiometry is to provide a steady potential against which to measure the working electrode half-cell (for example, an ion-selective electrode, redox potential electrode or enzyme electrode). In amperometric techniques, two electrode cell configurations are widely used (working and counter electrode half-cells) but, particularly in more accurate work, three electrode cell configurations are used, where the reference electrode is used to provide a sample reference potential.

The most common types are calomel (using mercury/mercury chloride couple) and silver/silver chloride reference electrodes. Thus the metal electrode (Ag or Hg) is bathed in a halide salt solution, which is connected to the sample through some form of liquid junction, for example a porous ceramic frit.

The potential of the metal/metal halide couple within the device is used as the reference potential, on which is superimposed the potential of the liquid junction and any other potential exerted, for example, by the sample at the liquid junction. In order to maintain a steady potential, these reference electrodes usually contain a concentrated halide solution (for example, saturated potassium chloride), to minimise the variation in reference potential on diffusion of sample through the liquid junction into the inner halide solution. Further, the device is normally mounted so that the level of the inner filling solution is higher than that of the sample, so that the inner filling solution slowly leaks from the liquid junction, helping to maintain the inner filling solution and liquid junction with steady levels of electrolyte (i.e. the inner filling solution) and potential.

Particularly in the case of ion-selective electrodes (ISEs), rather than using a conventional reference electrode, another ion-selective electrode can be used as a reference against which the potential of the working ISE half-cell is measured. This approach requires that the activity (concentration) of the ion to which the "reference ISE" is selective, remains constant or changes in a known manner. Any other species in the sample which interferes with the "reference ISE" must also meet the same requirement. In most practical applications with complex and dynamically changing samples, this can be difficult or impossible to arrange. The approach is accordingly not widely used.

The main problems and disadvantages of conventional liquid-filled reference electrodes, with particular regard to ISE's, are believed to be:

i) comparatively large size (the liquid junction connection cannot, for example, be made smaller or of lower leakage without seriously affecting its performance);

ii) incompatibility with solid state working ISE manufacture processes and application configurations;

iii) leakage of strong/concentrated internal electrolyte changing the sample (for example, KCl leakage in $K^+$ determination);

iv) fouling or blockage of porous ceramic frit or other liquid junction;

v) replacement or topping-up of internal electrolyte solutions and other servicing required relatively frequently;

vi) possible variation in liquid junction potential with changes in the sample electrolyte concentration/ionic strength;

vii) poor impedance matching of the reference electrode (few Kilohm) to the working ISE (often Megohm to Gigohm), encouraging series mode electrical interferences and drift.

Attempts have been made to produce solid state or miniaturised versions of the above reference electrode. Essentially, the Ag/AgCl electrodes are overcoated with a hydrophilic polymer gel containing the internal electrolyte (for example, KCl) and some form of porous membrane or frit is then introduced. The main additional problems and limitations of these approaches are:

a) the reservoir of internal electrolyte is much smaller and its concentration therefore more easily changed by the sample;

b) it is most often difficult or impossible to ensure that internal electrolyte leaks from the device at a sufficient rate to maintain a steady potential at the liquid junction;

c) there is often a rapid drying out of the device which changes electrolyte concentrations, leading to salting-up of the junction and ultimately causing device failure.

For these reasons, and especially in extended storage or use, such solid state devices will be likely to drift or fail. Particularly in the case of disposable "one shot" tests, some have partially circumvented these problems by adjusting the internal electrolyte solution to be the same as the sample (usually a lower concentration) and placing the same electrolyte solution in a gel layer mounted outside the liquid junction. The latter layer is then removed immediately prior to contact with the sample. Electrolyte equilibration between the sample and reference electrode thereby becomes less problematical. The technique is not however capable of wide application.

SUMMARY OF THE INVENTION

It is an object of this invention to provide an improved reference electrode in which the above discussed problems and disadvantages are overcome either entirely or in large measure.

Accordingly, the present invention consists in one aspect in a reference electrode for use in determining the activity or concentration of an ionic species in a sample, in combination with a working electrode having a selective membrane responsive, by virtue of a selective component of that membrane, selectively to said ionic species and an internal electrode electrochemically coupled with said membrane, the reference electrode comprising a reference membrane which is of the same composition as the selective membrane save that said selective component is absent.

Advantageously, the reference membrane presents to the sample substantially the same external configuration as the membrane of the working electrode.

Preferably, the reference electrode is adapted for use with a working electrode comprising a membrane containing an appropriate ionophoric or ion binding compound, the reference membrane being substantially identical with said membrane save that the said compound is not present.

Thus it can be seen that in an important example of the present invention, a reference electrode is constructed in a similar or the same manner as the working ISE half-cell, but omitting the chemical elements which impart the permselectivity for a particular ion; the principle being that the reference electrode should as close as possible match the working ISE half-cell in physical, dimensional, electrochemical, physiochemical and chemical terms.

In another aspect, the present invention consists in an electrochemical cell for use in determining the activity or concentration of an ionic species in a sample contained within the cell, the cell comprising a working electrode having a selective membrane responsive by virtue of a selective component of that membrane, selectively to said ionic species, with an internal electrode electrochemically coupled with said membrane and a reference electrode comprising a reference membrane which is of the same composition as the selective membrane save that said selective component is absent.

In still a further aspect, the present invention consists in a method of electrochemically determining the activity or concentration of an ionic species in a sample, comprising measuring the potential developed between a working electrode and a reference electrode both in contact with the sample, the working electrode and reference electrode having substantially identical membranes save only that the membrane of the working electrode but not the membrane of the reference electrode comprises a selective component by virtue of which the membrane of the working electrode exhibits a selective response to the ionic species.

The reference electrode according to this invention may be regarded as a device with a membrane devised to lack significant ion permselective response, normally effected by incorporation of ionophoric or ion binding compounds, but which possess the complex potentiometric responses to changes in sample composition according to electrochemical double layer theory. The latter responses are made as identical as possible to those superimposed on the working ion-selective electrode by ensuring that the composition of the reference electrode membrane, the physical construction and physical presentation to the sample of the reference electrode closely resembles that of the desired working ion-selective electrode.

In the past, the purpose of a reference electrode has been regarded as being to provide a steady potential against which to measure another potential or to reference another measurement. The optimal design for a reference electrode on this basis diverges from that of the working ISE half-cell.

The fact that the reference electrode potential, particularly at the liquid junction, can and does vary has hitherto been ignored or has become part of the accepted protocol of using such devices (for example, the application of appropriate corrections and the use of constant ionic strength sample mixtures). As noted, the potential may vary as a result of changes in the sample and its effect on the complex liquid junction potential, variation in composition of the internal electrolyte and superimposition of electrical noise (and drift) from the sample on the reference electrode potential.

The present inventors have, in contrast, accepted that these potential variations do occur and recognised that in order to determine the potential developed at the working ISE half-cell, in response to variations in specific ion, the most appropriate reference measurement is one which "sees" everything imposed on the working ISE half-cell, except the ionic potential measured. It may be noted that the term "reference electrode" is for this reason used in this specification in a manner which may not fully accord with the conventional definition.

Since the chemical components providing the permselectivity are often of the order of 1% or less of the composition of the permselective membrane, the reference electrode can be made almost identical to the working ISE half-cell.

The present invention arose from a mistake made by a technician in not adding to a membrane the chemical rendering the device permselective. Having discovered the error, the present inventors were surprised, from their knowledge of the electrochemical prior art, that such a device did not drift badly as there was little or no ionic contact with the medium. This is perhaps one reason why electrochemists have not examined it before. However, the difference in electrical impedance (reflecting ionic conductivity) between the "reference" membrane and the "ISE" membrane has been found to be relatively small.

In one example, a liquid membrane, polyvinylchloride ion selective electrode for cation selectivities (for example $K^+$) has the following membrane composition:

| | |
|---|---|
| PVC | 35 wt. % |
| plasticiser (eg dioctyl sebecate) | 65.5 wt. % |
| ionophore (eg valinomycin) | 1 wt. % |
| counter ion | 0.5 wt. % |

In accordance with the present invention, a reference electrode is provided with a membrane of the same composition except that the ionophore is omitted. Optionally the counter ion is also omitted. By way of explanation, a particularly common counter ion is tetraphenylborate(TPB). In a $K^+$ ISE, it is found that TPB itself can complex with $K^+$ and provoke a permselective response as well as acting as a counter ion. In such circumstances, both the counter ion and the ionophore should be omitted in order to produce a membrane which exhibits substantially no response to $K^+$. This effect is much less significant with $Na^+$ ions, in which case the counter ion need not be omitted.

The reference electrode is, in one example, identical with the ISE apart from the described differences in the membrane. Alternatively, the reference membrane could be applied to any of a wide range of known electrodes. One example is a conventional liquid filled reference electrode where the porous ceramic frit or other liquid junction is replaced by the reference membrane. Alternatively, the reference membrane could be applied to the coated wire or film electrode in one case with an aqueous internal reference electrolyte (for example Ag/AgCl/KCl in PVA) and in another case without a thermodynamically reversible internal electrode, the latter by direct coating of the membrane onto Pt, Ag or Au. Further examples are the Ag/Ag TPB internal reference element disclosed in co-pending International application no. PCT/GB88/00992 and known ion sensitive field effect transistors (ISFET's). Still further examples will occur to the skilled man.

As well as responding to the electrical interferences in the same way as the working ISE, and providing good common mode rejection at the electrochemical device level and in the electronic measurement circuit, the described reference electrode according to this invention also responds to other interferents of the working ISE nulling their effect. Particularly in the case of PVC liquid membrane devices, it has been found hitherto that the PVC membrane itself or the plasticising solvent it contains may interact with more hydrophobic or amplibhilic ions which partition into or bind to the membrane. In the reference electrode according to this invention, both reference and working half-cells respond similarly and this effect is nulled.

Another effect of perhaps wider importance arises from the fact that varying the ionic composition of the sample will cause proportional variations in potential at any interface, according to electrochemical double layer theory. The magnitude of the potential variation would depend to a large extent upon the material properties of the interface and in a cell using a conventional reference electrode—with necessarily large differences between the sample interface at the working electrode and at the reference electrode, this effect can introduce significant error. According to the present invention, the working electrode and reference electrode sample interfaces are substantially identical such that this effect is again nulled. A similar effect which arises when flowing samples are employed is the development of streaming potentials, again based in double layer theory and having a significant dependence on the material properties, size and shape of the sample interface. These interferring potentials can again be nulled by the use of the present invention.

BRIEF DESCRIPTION OF THE DRAWINGS

The present invention will now be further described by way of examples and with reference to the accompanying drawings in which:

FIGS. 1(A)–4(B) schematically represent working and reference electrode pairs according to the present invention.

FIGS. 5(A) and 5(B) diagrammatically illustrates a process for producing a working and reference electrode pair as shown in FIG. 2.

DETAILED DESCRIPTION

Figure 1:
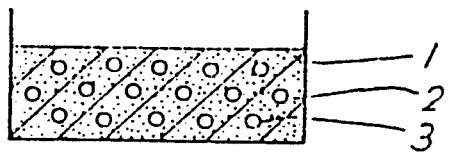
Figure 1:
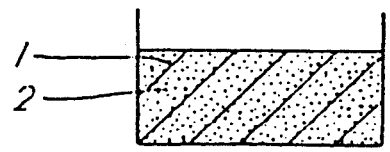

Referring to FIGS. 1A and 1B, the membrane of the working electrode A comprises a support polymer (1) plasticised with a solvent mediator (2) solvating the ion-sensing ligand or binding site (3). The membrane of the reference electrode B comprises the same support polymer (1) and plasticising solvent (2). The ion-sensing ligand or binding site of the working electrode is absent. In both cases, the plasticising solvent may also contain counter-ions.

Figure 2:
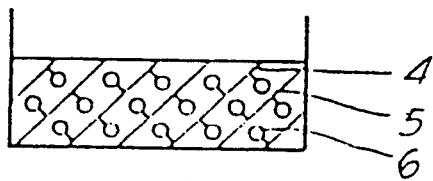
Figure 2:
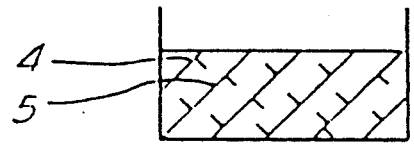

More particularly, the membranes may be formed as follows:

selective membrane:
36% poly(vinyl chloride)
63% di-octyl sebecate
1% valinomycin
reference membrane:
36.6% poly(vinyl chloride)
63.4% di-octyl sebecate In FIGS. 2A and 2B, the membrane of the working electrode A comprises a support polymer (4) chemically modified as depicted at (5) for attachment of ion-sensing ligands or binding sites (6). The membrane of the reference electrode B is constructed from support polymer (4) which is similarly chemically modified at (5) but which lacks ion-sensing ligands or binding sites. In both cases, the membrane may contain plasticising solvent.

In a more particular example, the membrane of the working electrode is poly-(vinyl Crown) and that of the reference electrode poly(styrene). A process for the production of poly-(vinyl Crown) is illustrated diagrammatically in FIG. 5(a), the structure of poly(styrene) being shown in FIG. 5(b) for comparison.

Figure 3:
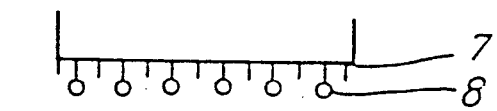
Figure 3:
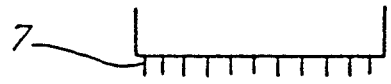

Turning to FIGS. 3A and 3B, the membrane of the working electrode A is constructed by chemically modifying a surface (7) and chemically attaching ion-sensing ligands (8). The reference membrane B is constructed by similar chemical modification of the same surface but with no attached ligand. A specific example is a glass surface with a Crown modified silane coating serving as the working electrode with an non-Crown modified silane as the inactive coating for the reference electrode.

Figure 6:
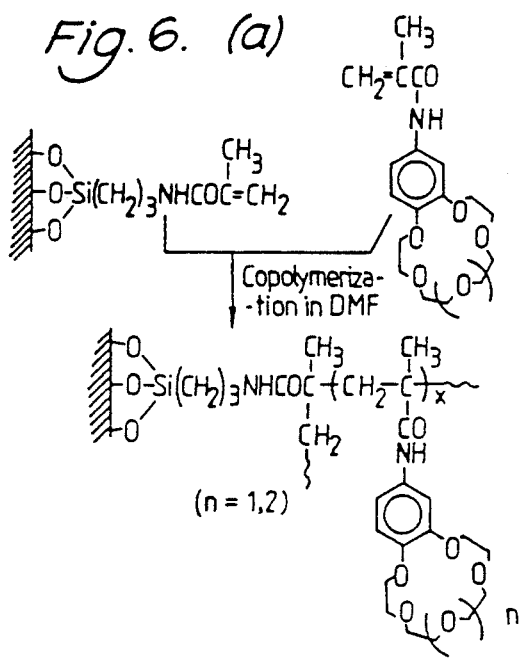
FIGS. 6(A) and 6(B) diagrammatically illustrates a process for producing a working and reference electrode pair as shown in FIG. 3.
Figure 6:
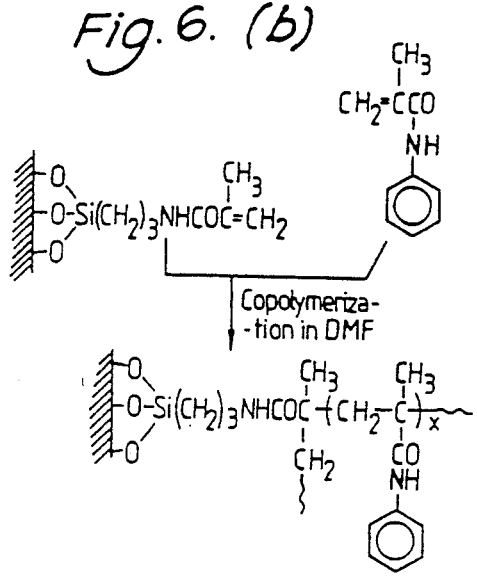

An example of a process for forming a Crown modified silane coating is illustrated diagrammatically in FIG. 6(a). Here, a surface 12 is first coated with a chemically bonded coating of a silane, with the silane being subsequently copolymerized in DMF with a Crown ether. FIG. 6(b) illustrates the related process for forming the non-Crown modified silane.

Figure 7:
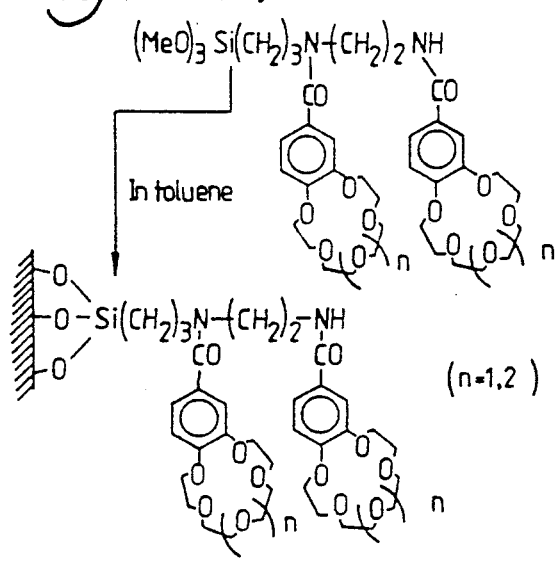
FIGS. 7(A) and 7(B) is similar to FIG. 6 and illustrates a modification.
Figure 7:
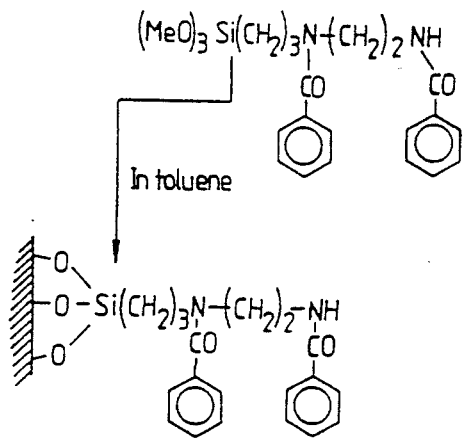

A further example is illustrated in FIG. 7(a) where a Crown modified silane compound in toluene is reacted directly with the surface 12. FIG. 7(b) shows the direct reaction of the analogous non-Crown modified compound.

Figure 4:
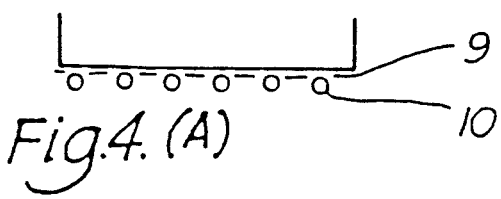
Figure 4:
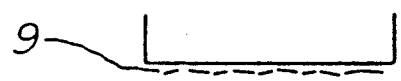

In the final example of FIGS. 4A and 4B, the membrane of the working electrode A is constructed by coating ion-sensing ligand (9) onto an appropriate surface with or without support material or polymer (10). The reference membrane B comprises the same surface with or without support material or polymer (10). Specifically, valinomycin is adhered to a graphite electrode structure with powdered PTFE as the support electrolyte material. To form the reference electrode, the PTFE powder, alone, is adhered to a like electrode structure.

It should be understood that in this specific description, and throughout the specification, the term "membrane" is used functionally as is conventional in the electrochemical field; no particular physical structure is implied by use of the term.

Figure 8:
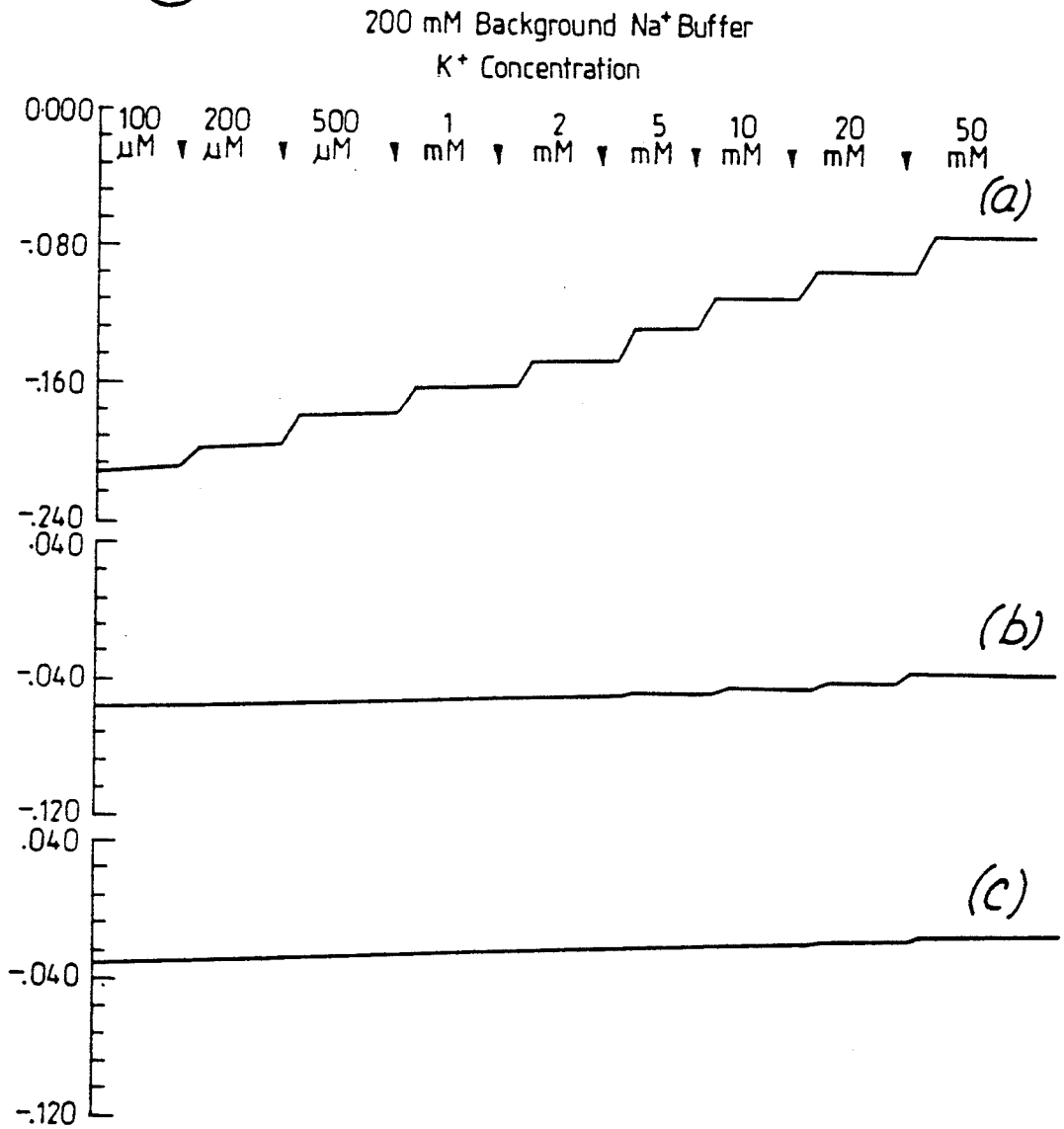
FIG. 8 shows graphically the response of an electrochemical cell according to this invention.

Referring to FIG. 8, there is shown graphically at (a) the typical response of a $K^+$ ion-selective electrode (using valinomycin, for example) measured against an inactive membrane reference electrode in accordance with this invention. The electrodes may, for example, be those shown in FIG. 1.

KCL is added stepwise to a background electrolyte solution comprising 100 nM $Na_2$borate buffer pH 7 (200 mM Na+). The final K+ concentration being shown at each step. Two further inactive membrane reference electrodes in the same electrolyte are connected with a conventional double junction Ag/AgCl reference electrode (Orion, USA). The responses of these further reference electrodes are shown in FIG. 8 at (b) and (c) respectively. They show the smaller non-spefific background response of the inactive membrane to additions of other ions (eg Na) and being primarily related to ionic strength. This response will occur also in the ion-selective membrane and in accordance with the invention, is effectively nulled.

It is believed that in its various forms, the present invention provides a number of important technical and commercial advantages. It becomes possible, for example, to produce a reference electrode of small size, whether the invention is applied to solid state or liquid filled devices. In the solid state form, the invention provides compatibility with solid state working ISE manufacturing processes and application configurations. The problems of leakage and contamination of the internal electrolyte are avoided along with the attendant problems of electrolyte replacement or topping-up and other frequent servicing requirements. The membrane is considerably less susceptible to fouling or blockage as compared with a porous ceramic frit. In addition to the "automatic" nulling of interferents, the present invention enables good impedance matching of the reference electrode to the working ISE, discouraging series mode electrical interferences and drift, thus providing good common mode rejection at the device level.

We claim:

1. A reference electrode for use in determining the activity or concentration of an ionic species in a sample, in combination with a working electrode having a selective membrane responsive, by virtue of a selective component of that membrane, selectively to said ionic species and an internal electrode electrochemically coupled with said membrane, the reference electrode comprising a reference membrane which is of the same composition as the selective membrane save that said selective component is absent.

2. A reference electrode according to claim 1, wherein the reference membrane presents to the sample substantially the same external configuration as the selective membrane of the working electrode.

3. A reference electrode according to claim 1, wherein the reference electrode is adapted for use with a working electrode comprising a selective membrane having an appropriate ionophoric or ion-binding compound, as the selective component, the reference membrane being identical with the selective membrane save that said compound is not present.

4. A reference electrode according to claim 1, wherein the reference membrane comprises a polymeric element and the selective membrane comprises a like polymeric element to which has been added appropriate ion-sensing ligand or binding sites.

5. A reference electrode according to claim 3, wherein the selective membrane comprises a surface to which is bound an ion-sensing ligand, the reference membrane comprising a like surface with no ion-sensing ligand.

6. An electrochemical cell for use in determining the activity or concentration of an ionic species in a sample contained within the cell, the cell comprising a working electrode having a selective membrane responsive by virtue of a selective component of that membrane, selectively to said ionic species, with an internal electrode electrochemically coupled with said membrane and a reference electrode comprising a reference membrane which is of the same composition as the selective membrane save that said selective component is absent.

7. An electrochemical cell according to claim 6, wherein the reference membrane presents to the sample substantially the same external configuration as the selective membrane of the working electrode.

8. An electrochemical cell according to claim 6, wherein the selective membrane includes, as the selective component, an appropriate ionophoric or ion-binding compound, the reference membrane being identical with the selective membrane save that the said compound is not present.

9. An electrochemical cell according to claim 6, wherein the reference membrane comprises a polymeric element and the selective membrane comprises the same polymeric element with appropriate ion-sensing ligand or binding sites.

10. An electrochemical cell according to claim 9, wherein the polymeric element of the selective membrane is chemically modified to receive the ion-sensing ligand or binding sites.

11. An electrochemical cell according to claim 8, wherein the selective membrane comprises a surface to which is bound an ion-sensing ligand, the reference membrane comprising a like surface with no ion-sensing ligand.

12. A method of electrochemically determining the activity or concentration of an ionic species in a sample comprising the steps of:
    contacting the sample with a working electrode and a reference electrode having identical membranes save only that the membrane of the working electrode but not the membrane of the reference electrode comprises a selective component, and
    measuring the potential developed between the working electrode and reference electrode.

* * * * *